US009165452B2

(12) United States Patent
Li et al.

(10) Patent No.: US 9,165,452 B2
(45) Date of Patent: Oct. 20, 2015

(54) DRIVER DROWSINESS PREDICTION SYSTEM AND METHOD THEREOF

(75) Inventors: Chia-Hsien Li, New Taipei (TW);
Yao-Tsung Chang, New Taipei (TW);
Pai-Yang Lin, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 23 days.

(21) Appl. No.: 13/611,487

(22) Filed: Sep. 12, 2012

(65) Prior Publication Data

US 2013/0207804 A1 Aug. 15, 2013

(30) Foreign Application Priority Data

Feb. 15, 2012 (TW) .............................. 101104943 A (51) Int. Cl.
*G08B 23/00* (2006.01)
*G08B 13/00* (2006.01)
(Continued)

(52) U.S. Cl.
CPC . *G08B 21/06* (2013.01); *A61B 5/04* (2013.01); *A61B 5/18* (2013.01); *G08G 1/096716* (2013.01); *Y02T 10/84* (2013.01)

(58) Field of Classification Search
CPC ...... G08B 21/06; Y02T 10/84; A61B 5/0476; A61B 5/16; A61B 5/7203; A61B 5/7257; A61B 5/021; A61B 5/0402; A61B 5/048; A61B 5/01; A61B 2503/22; A61B 5/0484; A61B 5/1103; A61B 5/18; A61B 5/7264; H01M 10/052; H01M 4/366; H01M 4/525; H01M 4/62; B60K 28/06; B60K 28/066; H04B 7/15557; H04L 27/2602; H04L 27/2607; H04L 5/001; G06F 19/3431; G06F 19/345; B60R 2325/101; B60R 2325/205; B60R 2325/302; B60R 25/102; B60R 25/305; B60R 2021/01322; B60R 2021/01184; B64D 2045/0045; B64D 45/0015; G01C 21/3469; H01L 21/28202; H01L 29/513; B60Q 9/008; B62D 1/046; B62D 1/06; G08G 1/096716
USPC ............... 340/575, 576, 691.1, 692; 180/443, 180/404, 446, 79.1, 133, 142; 128/639, 128/774, 782, 732, 739, 742, 905, 706, 630
See application file for complete search history.

(56) References Cited

U.S. PATENT DOCUMENTS 4,604,611 A * 8/1986 Seko et al. ..................... 340/576
5,311,877 A * 5/1994 Kishi ............................. 600/545
(Continued)

FOREIGN PATENT DOCUMENTS

CN 101243973 A 8/2008
CN 201654537 U 11/2010
(Continued)

OTHER PUBLICATIONS

Chinese Office Action for Chinese Application No. 20120045672.5 dated Sep. 28, 2014 with English translation.

*Primary Examiner* — Mirza Alam
(74) *Attorney, Agent, or Firm* — Muncy, Geissler, Olds & Lowe, P.C.

(57) ABSTRACT

A driver drowsiness prediction system includes a vital signal detection unit, a control unit and a network bridge module. The vital signal detection unit detects vital signals of a driver. The control unit receives the driver's vital signs, and stores at least a feature signal. The feature signal represents the vital signal pattern of losing consciousness. The control unit continuously compares the detected vital signal with the feature signal. When the vital signal is similar to the feature signal, the control unit issues a pre-alarming command. The network bridge module receives the pre-alarming command and is triggered to perform a network connection process. The network bridge module logs into a pre-determined social website according to a login script, and then sends a pre-alarming message thereon, wherein the pre-alarming message includes an event indicating the driver is near unconsciousness.

26 Claims, 6 Drawing Sheets

(51) Int. Cl.
  *B60K 28/00* (2006.01)
  *B60R 21/00* (2006.01)
  *G08B 21/06* (2006.01)
  *A61B 5/18* (2006.01)
  *G08G 1/0967* (2006.01)
  *A61B 5/04* (2006.01)

(56) References Cited

U.S. PATENT DOCUMENTS

| | | | |
|---|---|---|---|
| 5,813,993 A * | 9/1998 | Kaplan et al. | 600/544 |
| 2003/0137426 A1 * | 7/2003 | Anthony et al. | 340/574 |
| 2005/0021204 A1 * | 1/2005 | Kudo | 701/36 |
| 2005/0190062 A1 * | 9/2005 | Sullivan et al. | 340/573.1 |
| 2009/0184828 A1 * | 7/2009 | Speller | 340/575 |
| 2009/0259138 A1 | 10/2009 | Lin et al. | |
| 2011/0118619 A1 * | 5/2011 | Burton et al. | 600/544 |
| 2012/0154156 A1 * | 6/2012 | Kuntzel | 340/575 |

FOREIGN PATENT DOCUMENTS

| | | |
|---|---|---|
| CN | 101927781 A | 12/2010 |
| TW | M363417 | 8/2009 |
| TW | 200943204 A | 10/2009 |
| TW | M371933 U1 | 1/2010 |
| TW | 201117598 A | 5/2011 |

* cited by examiner

DRIVER DROWSINESS PREDICTION SYSTEM AND METHOD THEREOF

CROSS-REFERENCES TO RELATED APPLICATIONS

This non-provisional application claims priority under 35 U.S.C. §119(a) on Patent Application No. 101104943 filed in Taiwan, R.O.C. on 2012 Feb. 15, the entire contents of which are hereby incorporated by reference.

BACKGROUND

1. Technical Field

The disclosure relates to a vital signal detection system, and more particularly to a driver drowsiness prediction system and method thereof.

2. Related Art

Driver fatigue is one of the major reasons for traffic accidents. When fatigued, the driver usually enters a dozing condition, resulting in traffic accidents.

Figure 1:
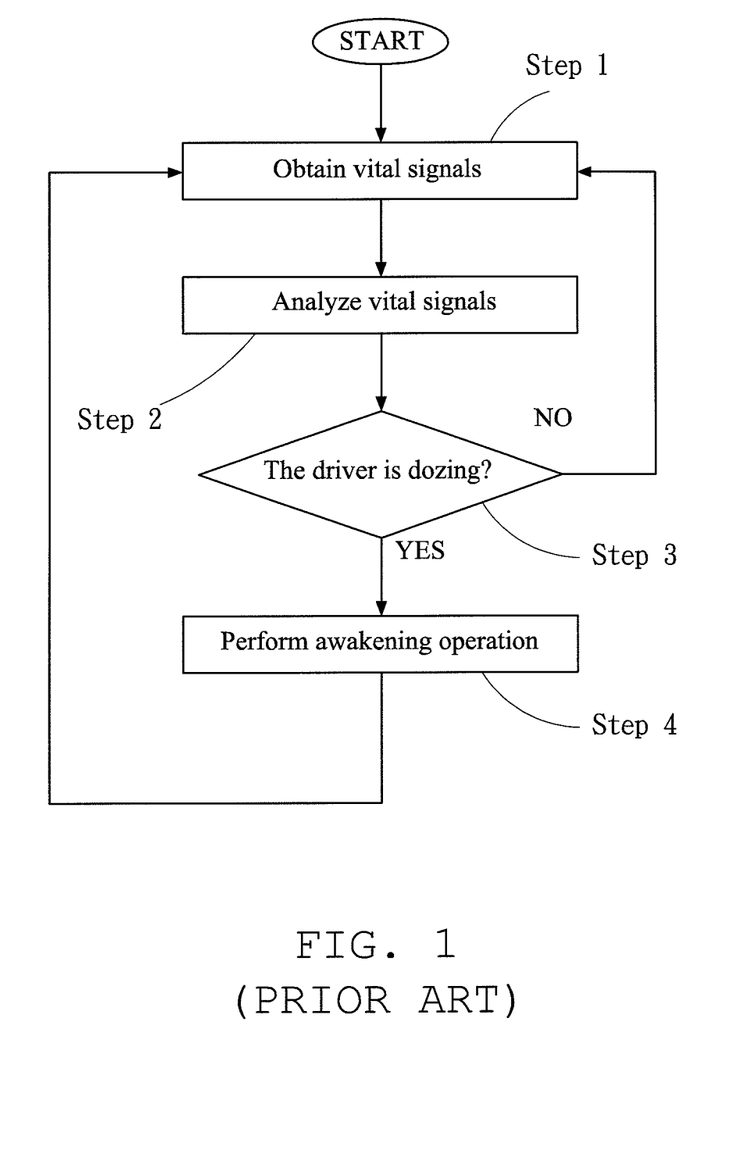
FIG. 1 is an explanatory flow chart of an awakening process according to a conventional technology.

FIG. 1 shows a basic process for a drowsiness preventing system in the conventional technology. Such a drowsiness preventing system must obtain and further analyze the driver's vital signs, as shown in Step 1 and Step 2. Such a drowsiness preventing system determines if the driver is dozing according the analysis result of the vital signals, as shown in Step 3. If the driver is dozing, such a drowsiness preventing system performs an awakening operation to awaken the driver, as shown in Step 4.

In the conventional technologies, the methods to detect drowsiness of a driver include: motion detection of the driver's head, as mentioned in Taiwan patent No. M363417; detection of the driver's eye blinking frequency; and detection of brain waves, as mentioned in U.S. Pat. No. 5,813,993. Among these methods, since the detections of the driver's head and the driver's eye blinking frequency usually have misjudging problems, drivers are unwilling to use such types of anti-drowsiness systems. The detection of brain waves has relatively higher accuracy since such method is adjustable according to the characteristics of brain waves of different individuals.

As shown in FIG. 1, even though Step 4 performs the awakening operation, such an awakening operation does not guarantee keeping the driver awake, and others cannot provide any assistance either. Consequently, the awakening processes shown in FIG. 1 still has the risk of failing to awaken the driver, and allowing the driver to keep dozing off

SUMMARY

Aiming at the driver awakening process in the conventional technology and the risk of failing to awaken a driver and instead allowing the driver to keep dozing off, a driver drowsiness prediction system and method are provided to effectively reduce the probability of the driver's drowsiness.

In one or more embodiments, a driver drowsiness prediction system is adapted to detect the consciousness statuses of a driver, and is able to give an alarm if the driver is near unconsciousness. The system includes a vital signal detection unit, a control unit and a network bridge module.

The vital signal detection unit detects the driver's vital signs. The control unit receives the vital signals and stores a feature signal therein. The feature signal represents a vital signal pattern when the driver is near unconsciousness. The control unit continuously compares the vital signals detected by the vital signal detection unit with the feature signal, and the control unit issues an pre-alarming command when the vital signal is identical or similar to the feature signal.

The network bridge module receives the pre-alarming command, performs a network linking operation, logs in a pre-determined social website according to a login script, and then sends a pre-alarming message; the pre-alarming message includes an event indicating the driver is near unconsciousness.

In one or more embodiments, a driver drowsiness prediction method is adapted to be detectable on conscious statuses of a driver and alarmable if the driver is near unconsciousness. The method includes: receiving the driver's vital signs; analyzing the vital signals; determining whether the driver is near unconsciousness; and when the driver is near unconsciousness, performing a network linking operation, logging in a pre-determined social website according to a login script, and then sending a pre-alarming message, wherein the pre-alarming message includes an event indicating the driver is near unconsciousness.

The disclosed system and method mainly start to perform an awakening operation when the driver is near unconsciousness, such that the problem after the driver totally lost consciousness is able to be prevented. In the meantime, through the application of the social website, external designated receivers are able to help awaken the driver in case the in-automobile awakening means cannot perfectly awaken the driver.

BRIEF DESCRIPTION OF THE DRAWINGS

The disclosure will become more fully understood from the detailed description given herein below for illustration only, and thus not limitative of the present invention, wherein.

DETAILED DESCRIPTION

Figure 2:
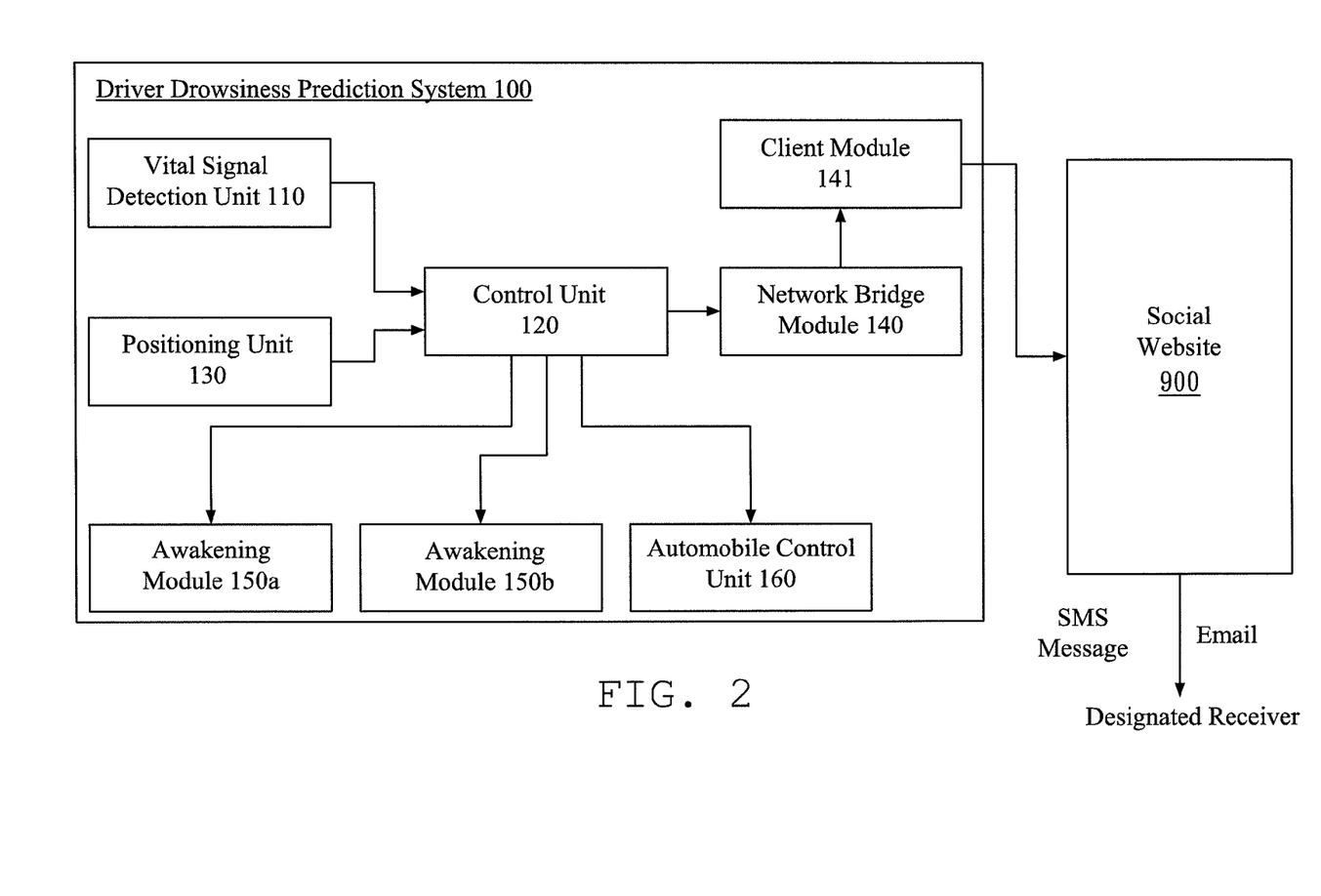
FIG. 2 is an explanatory system block diagram of a driver drowsiness prediction system according a first embodiment of the disclosure.

Please refer to FIG. 2, which is an explanatory system block diagram of a driver drowsiness prediction system according a first embodiment of the disclosure. The driver drowsiness prediction system is adapted to be detectable on conscious statuses of a driver and alarmable if the driver is near unconsciousness.

As shown in FIG. 2, a driver drowsiness prediction system 100 includes a vital signal detection unit 110, a control unit 120, a positioning module 130, a network bridge module 140, one or more awakening module 150a, 150b and an automobile control module 160. The vital signal detection unit 110, positioning module 130, network bridge module 140, awakening module 150a, 150b and automobile control module 160 are connected with control unit 120 through wired connection or wireless connection; wireless connection includes Bluetooth communication protocol, 2.4 GHz radio frequency or wireless AD-Hoc network.

As shown in FIG. 2, the vital signal detection unit 110 is used to detect and measure the driver's vital signs, especially those vital signals that are highly correlative to the driver's fatigue. In a first embodiment, the vital signal mainly includes brainwaves, and the vital signal detection unit 110 is realized by a brainwave instrument. The sensors of the brainwave instrument are realized by electrode pads attached onto the driver's temples; or the brainwave instrument is a head-mounted type tied on the driver's head with its sensors contacting thereto.

As shown in FIG. 2, the control unit 120 receives the vital signals detected or measured by the vital signal detection unit 110. In an embodiment, control unit 120 is a functional module realized by special-made hardware or software. For example, the control unit 120 may be realized by a mobile communication device that performs a control program; alternatively, control unit 120 is an independent computing chip designed by the required functions in the disclosure.

The control unit 120 stores one or more feature signals. The feature signal includes or represents a vital signal pattern when the driver is near unconsciousness. The control unit 120 continuously compares the vital signals obtained by the vital signal detection unit 110 with the feature signal. When the vital signal is similar to the feature signal, the control unit 120 determines that the driver is near unconsciousness, and issues a pre-alarming command.

Brainwaves are taken as examples to explain the ways of comparing the vital signals and the feature signal. Based on different frequency, brainwaves may be classified into α wave at 8-14 Hz, β wave at 14 Hz, θ wave at 4~8 Hz, and δ wave at 0.4~4 Hz. The four types of brainwave patterns are generated at the same time with different intensity; among which the stronger brainwave is called superior brainwave. When a person has lost consciousness with their body deeply relaxed, the superior brainwave is θ wave at 4~8 Hz; when the superior brainwave is δ wave at 0.4~4 Hz, the person is in a unconscious deep sleep; when the superior brainwave is β wave higher than 14 Hz, the person is having nervous emotion and remaining awake; when the superior brainwave is α wave at 8~14 Hz, the person stays awake yet their brainwaves could possibly transfer into 4~8 Hz superior θ brainwave at anytime, resulting in loss of consciousness.

In this embodiment, the feature signal includes a brainwave frequency range with its values between 8~9 Hz. A 8~9 Hz brainwave frequency range is nearly a θ wave; if θ wave becomes the superior brainwave, namely the driver has lost consciousness and possibly starts to doze off anytime. When the superior brainwave of the actual obtained brainwave is at 8~9 Hz, the actual obtained brainwave is determined to be similar to the feature signal, and the driver is determined near unconsciousness. In one or more of the embodiments, before the superior brainwave completely transforms in to θ wave, the system or method has started to perform pre-alarming and awakening operations. The aforesaid 8~9 Hz brainwave frequency range is for explanation purposes only, the practical value range is adjustable higher or lower according to variations in different drivers.

As shown in FIG. 2, the positioning module 130 receives multiple positioning signals sent from multiple positioning signal sources, such as positioning signals transmitted from a GPS (Global Positioning System), satellite, which is able to be transformed into positioning coordinate(s).

As shown in FIG. 2, the network bridge module 140 receives the pre-alarming command, performs a network linking operation and controls a client module 141. The client module 141 is a software functional module, adapted to log in a pre-designated social website 900 and perform a message posting function of social website 900 to generate "News Feed" thereof, thereby allowing a specific or non-specific third party to obtain the message sent from the driver drowsiness prediction system onto the social website 900.

Through the client module 141, the network bridge module 140 logs into a pre-determined social website 900 according to a login script, thereby sending a pre-alarming message on the social website 900 or through the social website 900. The pre-alarming message includes an event indicating the driver is near unconsciousness. The network bridge module 140 is able to further attach a geographic position of the driver within the pre-alarming message; the geographic position of the driver is indicated in map information according to the positioning coordinate(s) obtained from the positioning module 130.

The network mentioned previously is realized by communication networks such as the internet, GPRS (General Packet Radio Service), GSM (Global System for Mobile Communications), PSTN (Public Switched Telephone Network), 3G (3rd Generation) Communication Technology, 3.5G (3.5th Generation), Communication Technology, etc.

According to the message posting function and the login script of the social website 900, the pre-alarming message is able to be a "public" message; after sent and posted on the social website 900, the pre-alarming message is reviewable by any member with a general authority. The posted pre-alarming message is able to be a "private" message; namely the pre-alarming message posted on the social website 900 is reviewable by only designated receiver(s) or other designed group(s).

Through the communication functions of the social website 900, after pre-alarming message is sent from the network bridge module 140 to the social website 900, the sent pre-alarming message is posted on or sent through the social website 900, or a message correlative to the pre-alarming message is sent through the social website 900 to a designated receiver(s) or designated group(s). For example, the pre-alarming message is sent through the social website 900 as SMS (Short Message Service), message or email to the mobile communication device or email account of the designated receiver, to suggest the designated receiver contacting and awaken the driver. Other message correlative to the pre-alarming message includes indicating the driver's geographic position in map information; if the designated receiver cannot successfully contact the driver, through the driver's geographic position indicated on the map information, the designated receiver is able to contact a third party (such as police officers), and ask for further supports.

Through the applications of social website 900, the designated receiver outside the automobile is to help awaken the driver, thereby overcoming the problem that the in-automobile awakening means is unable to awaken the driver perfectly.

As shown in FIG. 2, the awakening modules 150a, 150b connects with the control unit 120 to receive the pre-alarming command and perform an awakening operation. Multiple awakening modules 150a, 150b are able to perform different awakening operations, such as outputting alarming sounds, vibrations, alarming lights and outputting an instruction requesting the driver's response to at least one of the outputs. These awakening operations are performable by different awakening modules 150a, 150b; alternatively more than two awakening operations are provided by the same awakening module.

As shown in FIG. 2, the automobile control module 160 receives the pre-alarming command and performs an automobile control operation. The automobile control operation includes detecting a moving direction of the automobile, adjusting the moving direction and alerting to other automobiles. The methods of alerting to other automobiles include alerting through flickering automobile alerting lamps or through an automobile horn.

Figure 3:
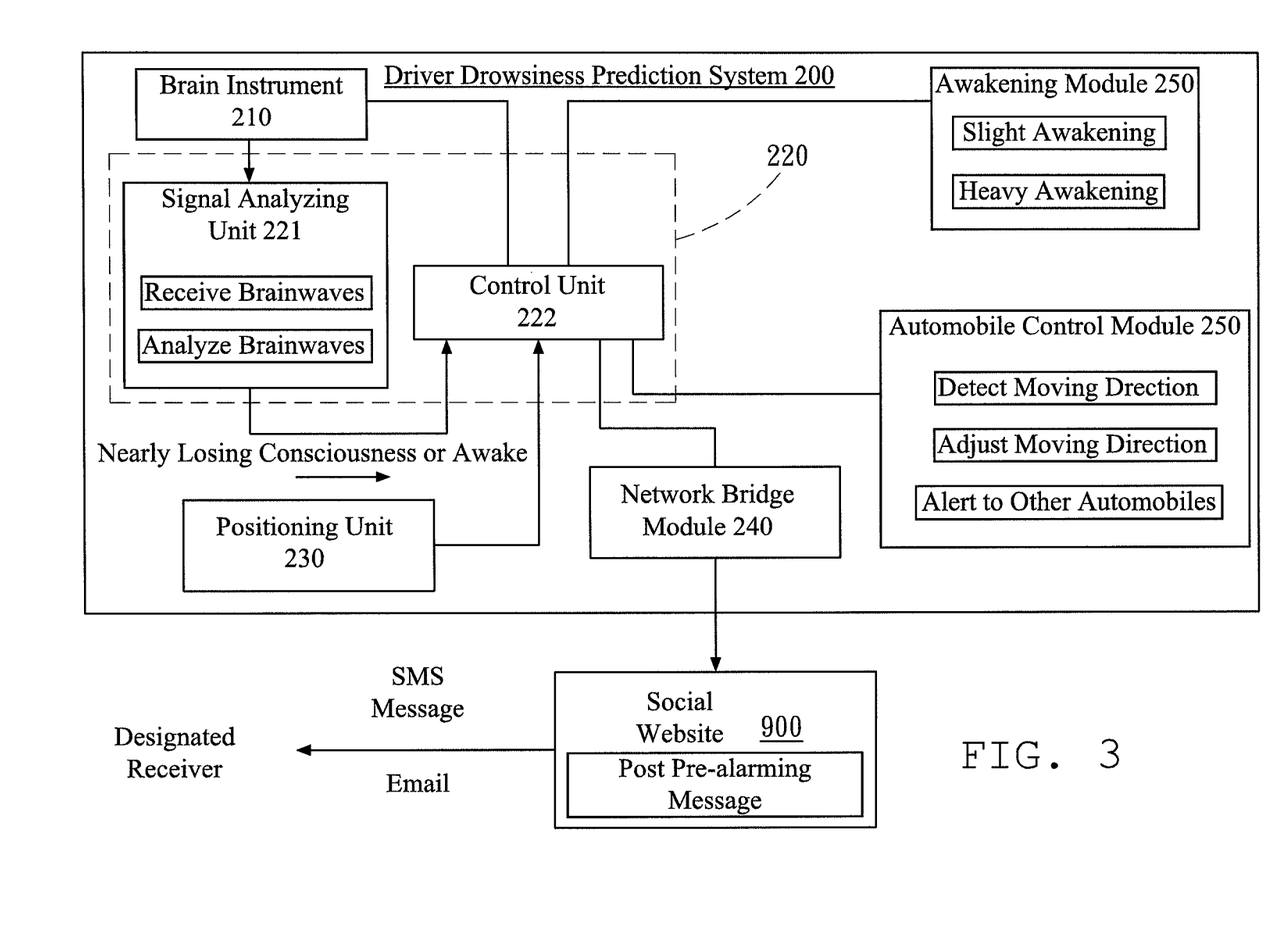
FIG. 3 is an explanatory system block diagram of another driver drowsiness prediction system according a second embodiment of the disclosure.

Please refer to FIG. 3, which is an explanatory system block diagram of another driver drowsiness prediction system according a second embodiment of the disclosure driver. A drowsiness prediction system 200 is adapted to be detectable on conscious statuses of a driver and alarmable if the driver is near unconsciousness. The driver drowsiness prediction system 200 includes a brainwave instrument 210, a control unit 220, a positioning module 230, a network bridge module 240, an awakening module 250 and an automobile control module 260; wherein, the control unit 220 includes a signal analyzing unit 221 and a controller 222.

As shown in FIG. 3, the brainwave instrument 210 is to measure the driver's brainwaves; the brainwave instrument 210 connects with the signal analyzing unit 221 to send brainwaves to the signal analyzing unit 221.

The signal analyzing unit 221 receives and analyzes the brainwaves, so as to determine whether the driver is near unconsciousness or remains awake. The signal analyzing unit 221 stores one or more feature signals, and the signal analyzing unit 221 bases on the feature signal to perform signal analysis on the brainwave signals, such that the driver is determined near unconsciousness or remaining awake and the determining results are sent to the controller 222. The controller 222 receives the determining results; when the determining result indicates that the driver is near unconsciousness, the controller 222 issues a pre-alarming command. The analyzing methods for the brainwaves are as introduced in the first embodiment.

As shown in FIG. 3, the positioning module 230 is to receive positioning signals transmitted from multiple positioning signal sources, and transform the positioning signals into positioning coordinate(s). The network bridge module 240 is able to receive the pre-alarming command, perform a network linking operation, log in a pre-determined social website 900 according to a login script, and then sends a pre-alarming message; wherein the pre-alarming message includes an event indicating the driver is near unconsciousness. The network bridge module 240 is able to further attach a geographic position of the driver within the pre-alarming message; the geographic position of the driver is indicated in map information according to the positioning coordinate(s) obtained from the positioning module 230.

Through the communication functions of the social website 900, the social website 900 further sends the pre-alarming message or a message correlative to the pre-alarming message through SMS (Short Message Service), message or email to the mobile communication device or email account of the designated receiver, to suggest the designated receiver contacting and awaken the driver. The designated receiver that receives the pre-alarming message or the correlative message is able to contact and confirm the status of the driver through his mobile communication device.

As shown in FIG. 3, the awakening module 250 connects with the controller 222, receives the pre-alarming command and performs an awakening operation. Based on the awakening operation, the awakening module 250 first perform a slight awakening and waiting for the driver's awake responses. If the driver does not provide awakening responses in a certain period, the awakening module 250 further performs a severe awakening.

The awakening operations includes vibration awakening, such as actuating the vibrations of the driver's seat. The awakening module 250 is able to start with a slight vibration to hint the driver and ask the driver to input awakening responses such as a voice response, a specific key command or a specific operating gesture. After performing the awakening operation, the awakening module 250 further waits for an awakening response from the driver. If the driver does not input an awakening response in a certain period, the awakening module 250 further increases the vibration intensity to a severe awakening. In addition to generating vibrations, the slight/severe awakening include outputting alarming sound, slight electric shocks, alerting lights, or an instruction requesting the driver's response to at least one of the outputs. A shown in the first embodiment, the second embodiment includes multiple awakening modules 250, each performing different types of awakening operations, or performing more than two awakening operations through a single awakening module.

As shown in FIG. 3, the automobile control module 260 performs an automobile control operation after receiving the pre-alarming command. The automobile control operation includes detecting a moving direction of the automobile, adjusting the moving direction and alerting to other automobiles.

Figure 4:
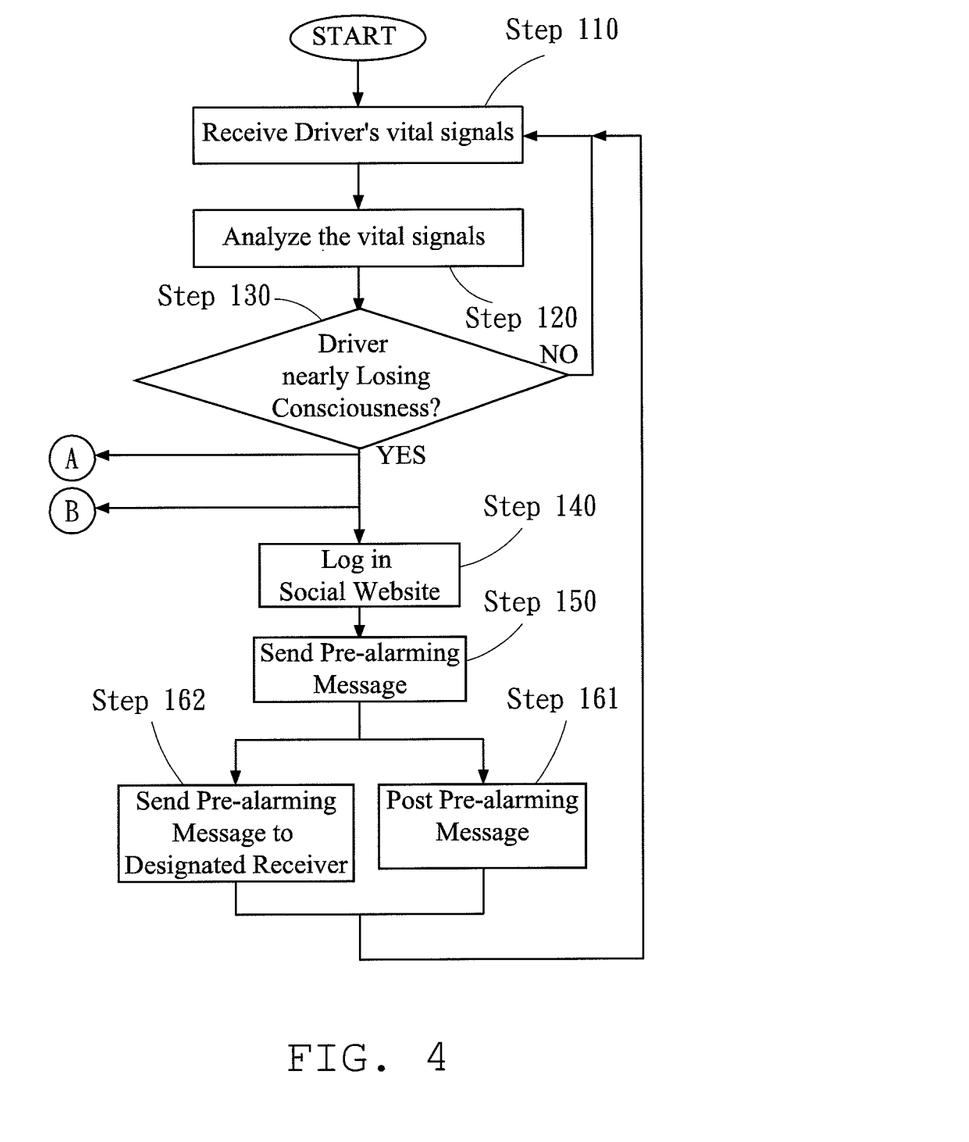
FIG. 4 is an explanatory flow chart of a driver drowsiness prediction method according the disclosure.

Please refer to FIG. 2 and FIG. 4 together; FIG. 4 is an explanatory flow chart of a driver drowsiness prediction method according the disclosure. The method is adapted to be detectable on conscious statuses of a driver and alarmable if the driver is near unconsciousness. The driver drowsiness prediction method includes the following steps.

Receive the driver's vital signals through the vital signal detection unit 110, as shown in Step 110.

Receive the vital signals through the control unit 120 and analyze the vital signal, as shown in Step 120. The vital signals are brainwaves; the analysis methods of brainwaves are introduced as the first embodiment.

The control unit 120 determines whether the driver is near unconsciousness, as shown in Step 130. If the driver is not near unconsciousness, return back to Step 110: re-obtain and analyze the new vital signals.

If the driver is near unconsciousness, the network bridge module 140 performs a network linking operation, logs in a pre-determined social website 900 according to a login script, as shown in Step 140. After logging in the social website, the control unit 120 further controls the network bridge module 140 to send a pre-alarming message to the social website 900, as shown in Step 150.

The sent pre-alarming message is posted on the social website 900, as shown in Step 161; wherein the pre-alarming message includes an event indicating the driver is near unconsciousness. Furthermore, through the communication function of the social website 900, the pre-alarming message or a message correlative to the pre-alarming message is sent as SMS message or email through the social website 900 to a designated receiver, as shown in Step 162, to suggest the designated receiver contacting the driver.

The method further includes through the positioning module 130, obtain a positioning coordinate and bases on the positioning coordinate, indicated the driver's geographic position in map information. The driver's geographic position indicated in map information is processed as a message correlative to the re-alarming message and attached within the pre-alarming message.

Figure 5:
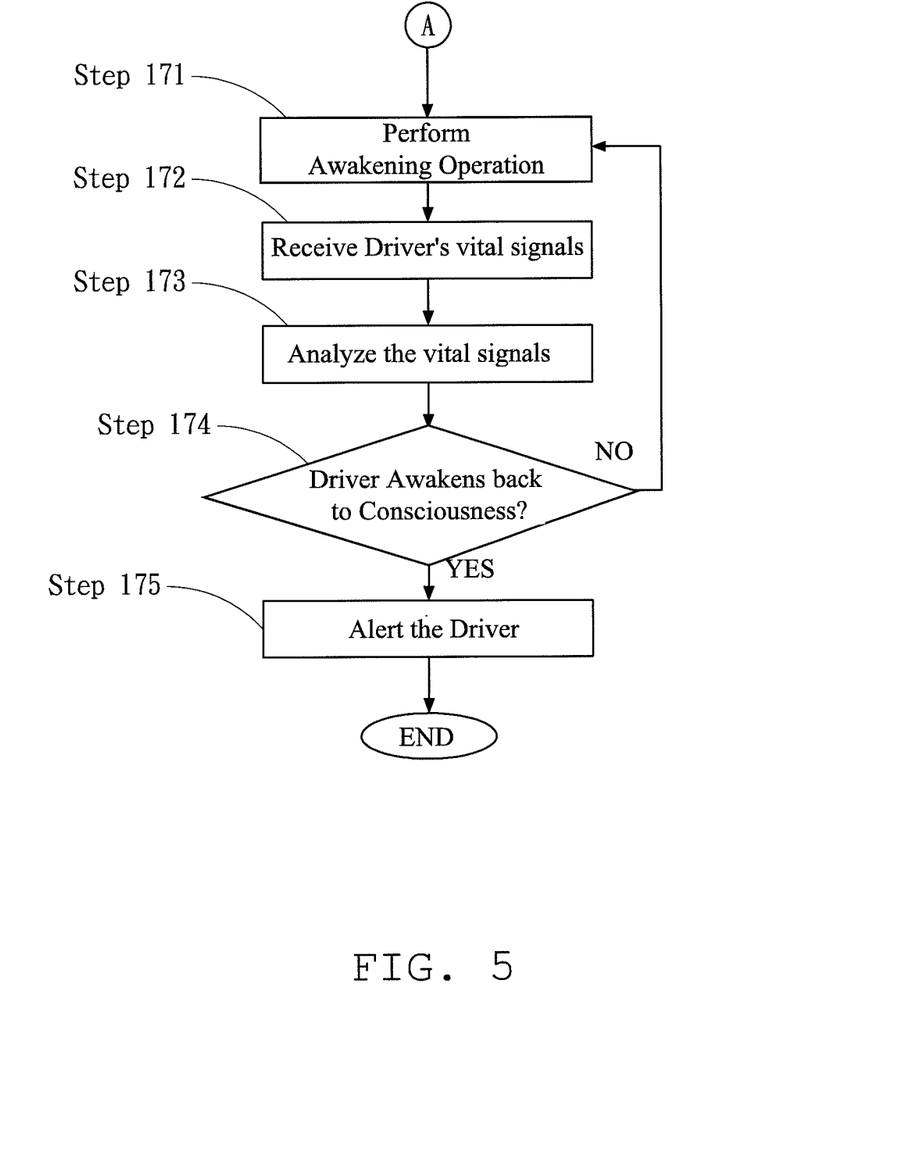
FIG. 5 is an explanatory flow chart of an awakening operation for a driver drowsiness prediction method according the disclosure.

As shown in FIG. 4 and FIG. 5, when the driver is near unconsciousness, the method performs an awakening operation through the awakening modules 150a, 150b, as shown in Step 171. The awakening operation includes include outputting alarming sound, slight electric shocks, alerting lights, or an instruction requesting the driver's response to at least one of the outputs. After performing the awakening operation, the method further receives and analyzes the driver's vital signal, as shown in Step 172 and Step 173. According to the result of analyzing the vital signals, determine whether the driver is returning to consciousness, as shown in Step 174. If the driver is determined to be returning to consciousness, further alert the driver to make him realize an event of his near unconsciousness is happening; so the driver is able to determine if they should continue driving, as shown in Step 175. If the driver does not return to consciousness, perform the awakening operation again, as shown in Step 171.

Figure 6:
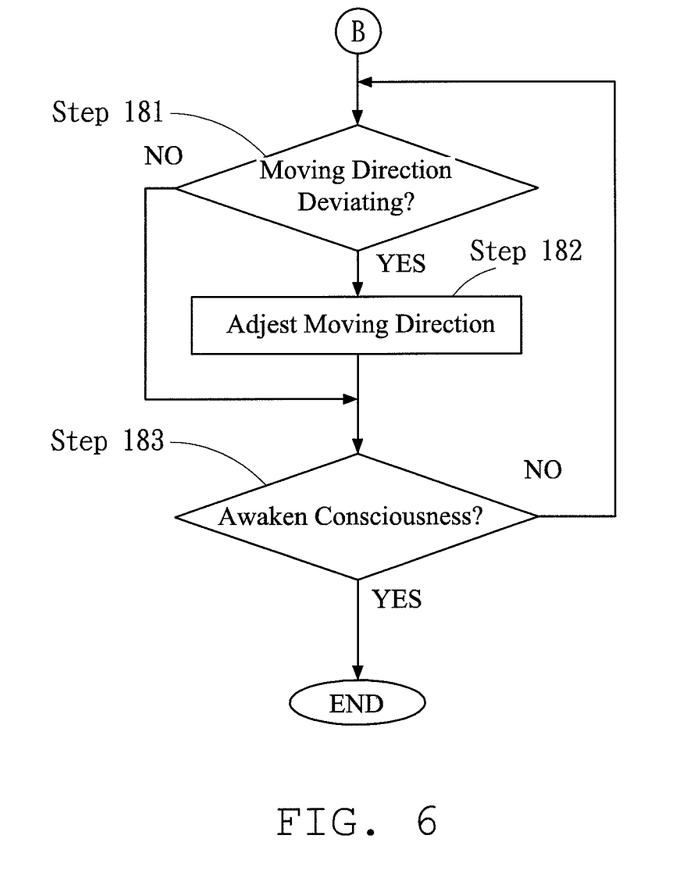
FIG. 6 is an explanatory flow chart of an automobile control operation for a driver drowsiness prediction method according the disclosure.

As shown in FIG. 4 and FIG. 6, when the driver is near unconsciousness, alternatively the method performs an automobile control operation through the automobile control module 160. The automobile control operation includes detecting if a moving direction of the automobile is deviating from the origin lane on the road, as shown in Step 181. If the moving direction is deviating, adjust the moving direction and alert to other automobiles, as shown in Step 182. After adjusting the moving direction, according to the determining results of the latest vital signals, determine whether the driver is returning to consciousness, as shown in Step 183. If the driver is returning to consciousness, terminate the automobile control operation; if the driver is not returning to consciousness, continuously determine whether the moving direction is deviating from the origin lane on the road, as shown in Step 181. Similarly, if in Step 181 the moving direction is determined to not be deviating, determine whether the driver is awake, as shown in Step 183.

The disclosed system and method mainly start to perform an awakening operation when the driver is near unconsciousness, such that the problem after the driver totally loses consciousness is able to be prevented. In the meantime, through the application of the social website, external designated receivers are able to help awaken the driver, in case the in-automobile awakening means cannot perfectly awaken the driver.

While the disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A driver drowsiness prediction system, adapted to be detectable on conscious statuses of a driver and alarmable if the driver is near unconsciousness, the system comprising:
   a vital signal detection unit, detecting a plurality of the driver's vital signals;
   a control unit, receiving the vital signals and storing at least a feature signal therein, the feature signal representing a vital signal pattern when the driver is near unconsciousness, wherein the control unit continuously compares the vital signals detected by the vital signal detection unit with the feature signal, and the control unit issues an pre-alarming command when the vital signal is identical or similar to the feature signal;
   at least an awakening module, to perform an awakening operation to awaken the driver in response to the pre-alarming command, and to wait for an awakening response provided by the driver for a period to determine an action according to the awakening response;
   a network bridge module, after receiving the pre-alarming command, the network bridge module performing a network linking operation and controlling a client module to log in a pre-determined social website according to a login script and then sending a pre-alarming message thereon, wherein the pre-alarming message comprises an event indicating the driver is near unconsciousness; and
   a positioning module,
   wherein the driver drowsiness prediction system is provided within a vehicle of the driver,
   wherein a person other than the driver, who is remote from the vehicle, is informed of the event via the pre-determined social website, and
   wherein the positioning module receives a plurality of positioning signals transmitted from a plurality of positioning signal sources and transforms into at least a positioning coordinate, according to the positioning coordinate, the network bridge module indicating a geographic position of the driver in map information and attaching within the pre-alarming message accordingly.

2. The driver drowsiness prediction system of claim 1, wherein the sent pre-alarming message is posted on the social website.

3. The driver drowsiness prediction system of claim 1, wherein sending the pre-alarming message comprises through the social website, sending the pre-alarming message or a message correlative with the pre-alarming message to a designated receiver, to suggest the designated receiver contacting the driver.

4. The driver drowsiness prediction system of claim 1, wherein the vital signal comprises brainwave and the vital signal detection unit comprises a brainwave instrument.

5. The driver drowsiness prediction system of claim 4, wherein the brainwave comprises a superior brainwave and the feature signal comprises a brainwave frequency range, the vital signal being defined similar to the feature signal when the superior brainwave matches the brainwave frequency range.

6. The driver drowsiness prediction system of claim 5, wherein the brainwave frequency range is within 8-9Hz.

7. The driver drowsiness prediction system of claim 1, wherein the control unit comprises a mobile communication device for performing a control program.

8. The driver drowsiness prediction system of claim 1, wherein the control unit comprises:
   a signal analyzing unit, receiving and analyzing the brainwave, to determine whether the driver is near unconsciousness or remaining awake; and
   a controller, issuing the pre-alarming command when the driver is near unconsciousness.

9. The driver drowsiness prediction system of claim 1 further comprising an automobile control module, the automobile control module performing an automobile control operation after receiving the pre-alarming command.

10. The driver drowsiness prediction system of claim 9, wherein the automobile control operation comprises detecting a moving direction, adjusting the moving direction and alerting to other automobiles.

11. The driver drowsiness prediction system of claim 1, wherein the awakening operation comprises outputting alarming sounds, vibrations, slight electric shocks, alarming lights and outputting an instruction requesting the driver's response to at least one of the outputs.

12. A driver drowsiness prediction method, adapted to be detectable on conscious statuses of a driver and alarmable if the driver is near unconsciousness, the method comprising:

provide a driver drowsiness prediction system within a vehicle of the driver;

receiving a plurality of the driver's vital signals;

analyzing the vital signals;

determining whether the driver is near unconsciousness;

when the driver is near unconsciousness, performing an awakening operation to awaken the driver and waiting for an awakening response provided by the driver for a period to determine an action according to the awakening response;

performing a network linking operation using a network bridge module of the driver drowsiness prediction system, logging in a pre-determined social website according to a login script by controlling a client module and then sending a pre-alarming message thereon, wherein the pre-alarming message comprises an event indicating the driver is near unconsciousness;

informing a person other than the driver, who is remote from the vehicle, of the event via the pre-determined social website;

obtaining a least a positioning coordinate; and according to the positioning coordinate, indicating a geographic position of the driver in map information and attaching within the pre-alarming message accordingly.

13. The driver drowsiness prediction method of claim 12, wherein the sent pre-alarming message is posted on the social website.

14. The driver drowsiness prediction method of claim 12, wherein the step of sending the pre-alarming message comprises through the social website, sending the pre-alarming message or a message correlative with the pre-alarming message to a designated receiver, to suggest the designated receiver contacting the driver.

15. The driver drowsiness prediction method of claim 12, wherein the vital signal comprises brain wave and the vital signal detection unit comprises a brainwave instrument.

16. The driver drowsiness prediction method of claim 15 further comprising a step of setting a brainwave frequency range, wherein the brainwave comprises a superior brainwave and the driver is defined near unconsciousness when the superior brainwave matches the brainwave frequency range.

17. The driver drowsiness prediction method of claim 16, wherein the brainwave frequency range is within 8-9Hz.

18. The driver drowsiness prediction method of claim 12 further comprising a step of performing an automobile control operation when the driver is near unconsciousness.

19. The driver drowsiness prediction method of claim 18, wherein the automobile control operation comprises detecting a moving direction, adjusting the moving direction and alerting to other automobiles.

20. The driver drowsiness prediction method of claim 12, wherein after performing the awakening operation, the method further comprises detecting whether the driver is returning to consciousness, and alarming the awakened driver.

21. The driver drowsiness prediction system of claim 1, wherein the awakening operation comprises a slight awakening and a severe awakening, the awakening module performs the slight awakening first, if the awakening module does not receive the awakening response in the period, the awakening module determines the action as performing the severe awakening.

22. The driver drowsiness prediction system of claim 1, wherein the awakening module determines the action as terminating the awakening operation if the awakening module receives the awakening response.

23. The driver drowsiness prediction system of claim 1, wherein the awakening response is selected from a group consisting of a voice response, a specific key command, and a specific operating gesture.

24. The driver drowsiness prediction method of claim 12, wherein the awakening operation comprises a slight awakening and a severe awakening, the slight awakening is performed first, if the awakening response is not received in the period, the action is determined as performing the severe awakening.

25. The driver drowsiness prediction method of claim 12, wherein the action is determined as terminating the awakening operation if the awakening response is received in the period.

26. The driver drowsiness prediction method of claim 12, wherein the awakening response is selected from a group consisting of a voice response, a specific key command, and a specific operating gesture.

* * * * *